United States Patent [19]

Behrens

[11] Patent Number: 4,942,163

[45] Date of Patent: Jul. 17, 1990

[54] 1(2H)-ISOQUINOLINONES AND 1-ISOQUINOLINEAMINES AS CANCER CHEMOTHERAPEUTIC AGENTS

[75] Inventor: Carl H. Behrens, Wilmington, Del.

[73] Assignee: E. I. Du Pont de Nemours and Company, Wilmington, Del.

[21] Appl. No.: 322,191

[22] Filed: Mar. 7, 1989

[51] Int. Cl.[5] .................. A61K 31/495; C07D 401/04
[52] U.S. Cl. ..................................... 514/254; 514/309; 514/310; 544/363; 546/141; 546/143
[58] Field of Search ................ 544/363; 546/141, 143; 514/254, 309, 310

[56] References Cited

U.S. PATENT DOCUMENTS 4,443,607  4/1984  Senda et al. .......................... 546/141
4,772,613  9/1988  Parsons et al. ....................... 546/141

Primary Examiner—Richard L. Raymond
Assistant Examiner—J. Turnipseed

[57] ABSTRACT

3-(1-Naphthalenyl)-1(2H)-isoquinolinones and 3-(1-naphthalenyl)-1-isoquinolineamines are useful as cancer chemotherapeutic agents.

40 Claims, No Drawings

1(2H)-ISOQUINOLINONES AND 1-ISOQUINOLINEAMINES AS CANCER CHEMOTHERAPEUTIC AGENTS

FIELD OF THE INVENTION

This invention relates to tumor inhibiting pharmaceutical compositions, methods of inhibiting the growth of mammalian tumors, and 1(2H)-isoquinolinones and 1-isoquinolineamine derivatives thereof useful in such compositions and methods.

BACKGROUND OF THE INVENTION

Isoquinolines are very well-known in the chemical literature. For example, the synthesis of isoquinolines has been comprehensively reviewed [Kametani et al.; *The Chemistry of Heterocyclic Compounds, Isoquinolines*, Vol. 38, Part 1, Chap. 2, J. Wiley & Sons, 1981, p. 139–274].

U.S. Pat. No. 3,912,740, issued to Zee-Cheng et al. on Oct. 14, 1975, discloses among others compounds of the formula

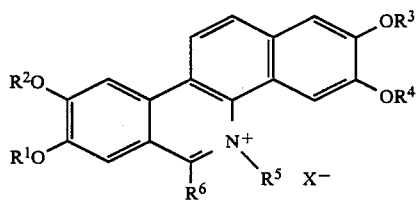

wherein
$R^1$, $R^2$, $R^3$ and $R^4$ independently are H, alkyl of 1 to 6 carbon atoms, or benzyl with the proviso that $R^1$ and $R^2$, or $R^3$ and $R^4$ taken together represent methylene;
$R^5$ is alkyl of 1 to 6 carbon atoms;
$R^6$ is H or alkoxy of 1 to 6 carbon atoms; and X is an anion.

These compounds are disclosed as having activity against murine L1210 leukemia and murine P388 leukemia.

U.S. Pat. No. 4,014,885, issued to Zee-Cheng et al. on Mar. 29, 1977, discloses compounds of the formula

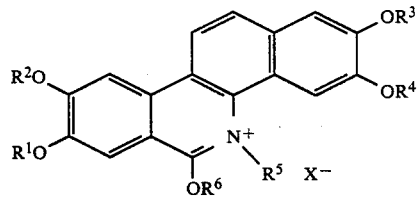

wherein $R^1$, $R^2$, $R^3$, $R^4$, $R^5$ and $R^6$ independently are H, alkyl of 1 to 6 carbon atoms, or benzyl, with the proviso that $R^1$ and $R^2$ taken together represent methylene.

Poindexter [J. Org. Chem., 47, 3787–3788 (1982)] reports the synthesis of 1(2H)-isoquinolinones by the reaction of the dilithium species derived from N,2-dimethylbenzamide with organic nitriles. No use for these compounds is described. Rose et al. [J. Chem. Soc. (C) 2205–2208 (1968)] reports the synthesis of 1(2H)-isoquinolinones by the reaction of ammonia with 3-arylisocoumarins. No use for these compounds is described.

The 1(2H)-isoquinolines of Formula (I) wherein X is O are prepared by a similar method involving the reaction of the monolithium species derived from substituted N,N,2-trimethylbenzamides with 1-cyanonaphthalene.

Pijper et al. [Eur. J. Med. Chem.-Chim. Ther. 19, 389–392 (1984)] and de Zwart et al. [J. Med. Chem. 31, 716–722 (1988)] report the synthesis and antimycoplasmal activity of 3-(2-pyridyl)-1-isoquinolineamines. Kaiser et al. [Synthesis, 805–806 (1974)], Van der Goot et al. [Eur. J. Med. Chem.-Chim. Ther. 10, 603–606 (1975); Eur. J. Med. Chem.-Chim. Ther. 7, 185–188 (1972)], and Wijbe in GB 1,173,227, issued on Dec. 3, 1969, report the synthesis of 1-isoquinolineamines by the reaction of the metalated species derived from 2-methylbenzonitrile with organic nitriles. This general method is used to prepare the compounds of this invention of Formula (I) wherein X is $NH_2$.

There are no known literature references disclosing the compounds of this invention or their use in the inhibition of mammalian tumors.

The compounds of this invention have in vitro and in vivo anticancer activity. As shown in Table 7, the compounds of this invention inhibit the growth of the RPMI-7272 human colon tumor cell line with $ID_{50}$'s ranging from 0.00077 μg/mL to 0.95 μg/mL. As shown in Tables 3 to 6, the compounds of this invention have significant anticancer activity in vivo in the L1210 murine leukemia, P388 murine leukemia, B16 murine melanoma, and/or LOX human amelanotic melanoma models.

SUMMARY OF THE INVENTION

This invention relates to tumor-inhibiting compounds of Formula (I), pharmaceutical compositions containing them, and methods of inhibiting mammalian cancers by administering such compounds.

The invention provides compounds of Formula (I):

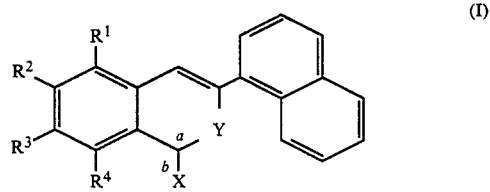

wherein
$R^1$ is H, $CH_3$, or Cl;
$R^2$ is H, $CH_3$, or Cl;
$R^3$ is $R^5$, Cl, $N(R^5)_2$, or $N^+(R^5)_3 I^-$ provided that, if X is $NR^6R^7$, $R^3$ is not $N(R^5)_2$ or $N^+(R^5)_3I^-$;
$R^4$ is H, $CH_3$, or Cl;
$R^5$ is H, or $C_1$ to $C_3$ alkyl;
X is O, or $NR^6R^7$; provided that, if X is O, a is a single bond, b is a double bond, and Y is NH, and, if X is $NR^6R^7$, a is a double bond, b is a single bond, and Y is N;
$R^6$ and $R^7$ independently are $R^5$, $(CH_2)_n N(R^5)_2$ where n is 2 to 8, or $R^6$ and $R^7$ taken together represent $-(CH_2CH_2)_2NR^5$;
and pharmaceutically acceptable salts thereof.

Preferred are the compounds of Formula I wherein
$R^1$ is H;
$R^2$ is H or $CH_3$; and
$R^4$ is H.

Specifically preferred are the compounds of Formula I wherein:

(a) (Ex. 1) $R^1=R^2=R^3=R^4=H$ and $X=O$; 3-(1-naphthalenyl)-1(2H)-isoquinolinone.

(b) (Ex. 2) $R^1=R^2=R^4=H$; $R^3=Cl$ and $X=O$; 7-chloro-3-(1-naphthalenyl)-1(2H)-isoquinolinone.

(c) (Ex. 3) $R^1=R^2=R^4=H$; $R^3=CH_3$ and $X=O$; 7-methyl-3-(1-naphthalenyl)-1(2H)-isoquinolinone.

(d) (Ex. 4) $R^1=R^2=R^4=H$; $R^3=N(CH_3)_2 \cdot HCl$ and $X=O$; 7-(dimethylamino)-3-(1-naphthalenyl)-1(2H)-isoquinolinone hydrochloride.

(e) (Ex. 20) $R^1=R^3=R^4=H$; $R^2=CH_3$ and $X=NH_2$; 6-methyl-3-(1-naphthalenyl)-1-isoquinolineamine.

(f) (Ex. 21) $R^1=R^2=R^4=H$; $R^3=Cl$ and $X=NH_2$; 7-chloro-3-(1-naphthalenyl)-1-isoquinolineamine.

(g) (Ex. 31) $R^1=R^2=R^4=H$; $R^3=CH_3$; and $X=$

7-methyl-1-(4-methyl-1-piperazinyl)-3-(1-naphthalenyl)-isoquinoline.

(h) (Ex. 40) $R^1=R^2=R^4=H$; $R^3=CH_3$; and $X=N(CH_3)CH_2CH_2N(CH_3)_2$; N,N,N'-trimethyl-N'-(7-methyl-3-(1-naphthalenyl)-1-isoquinolinyl)-1,2-ethanediamine.

DETAILED DESCRIPTION OF THE INVENTION

Synthesis

The compounds of Formula (I) wherein X is O can be prepared according to the route shown in Scheme 1. The amides of Formula (2) are prepared by coupling the carboxylic acids of Formula (1) with dimethylamine by methods which are well-known in the chemical literature. For example, the carboxylic acid (1) can be converted to the corresponding acid chloride with a reagent such as thionyl chloride or oxalyl chloride. The acid chloride can then be converted to the amide (2) by the reaction with aqueous dimethylamine under standard conditions. Alternatively, coupling agents such as dicyclohexylcarbodiimide, N,N'-carbonyldiimidazole, and the like, may be used in the reaction of the acids (1) with dimethylamine to form the amides (2).

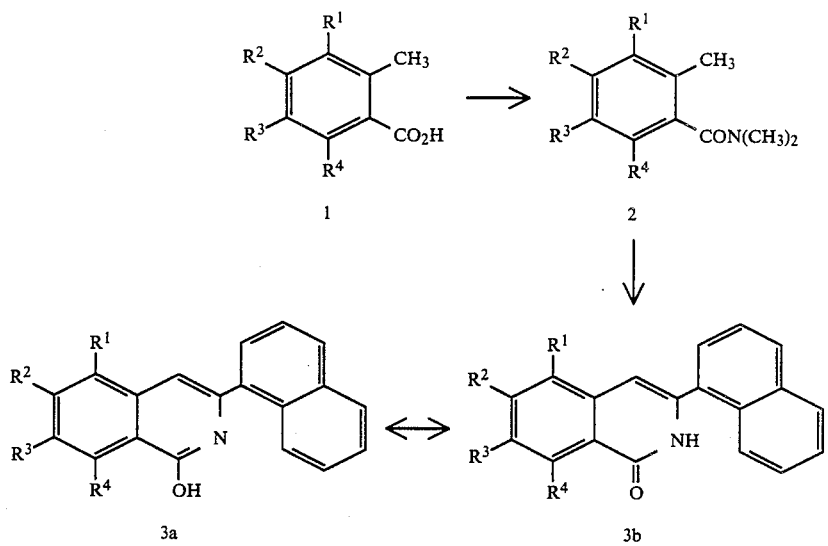

Scheme 1

Another approach to the amides of Formula (2) is by the ortho-metalation of an appropriate diethyl benzamide with s-butyllithium and tetramethylethylenediamine and subsequent alkylation with methyl iodide as described by Comins et al. [J. Org. Chem. 51, 3566–3572 (1986)].

The compounds of Formula (3) are prepared from the amides (2) by a one-pot procedure. The amide (2) is lithiated with lithium diisopropylamide in a suitable solvent such as tetrahydrofuran at a temperature from −78° to the boiling point of the solvent. The lithium salt reacts with 1-cyanonaphthalene to afford (3) by a mechanism which may involve 1,2-addition to the nitrile followed by intramolecular cyclization and tautomerization before or during the reaction workup. It is understood by those skilled in the art that the compounds of Formula (I) wherein X is O exist as an equilibrium mixture of the tautomers (3a) and (3b). The compounds of this invention of Formula (I) wherein X is O appear to exist predominantly in the tautomeric form (3b) on the basis of the presence of a strong carbonyl stretching absorption and the lack of a hydroxy stretching absorbtion in the infrared spectra of these compounds.

The compounds of Formula (I) wherein X is $NR^6R^7$ can be prepared according to the route shown in Scheme 2. The 1(2H)-isoquinolinones of Formula (3b) are converted to the 1-chloroisoquinolines of Formula (4) by the reaction with a reagent such as phosphorous oxychloride. The reaction of (4) with a primary or secondary amine of the formula $HNR^6R^7$ in the presence of a suitable base such as potassium carbonate in a suitable solvent such as dimethylformamide at a temperature from room temperature to the boiling point of the solvent affords the 1-isoquinolineamines of Formula (5).

Scheme 2

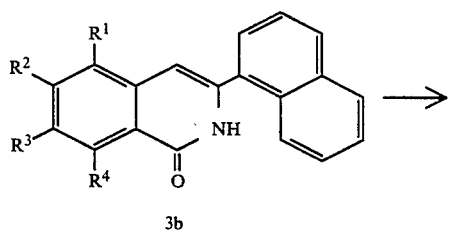

3b

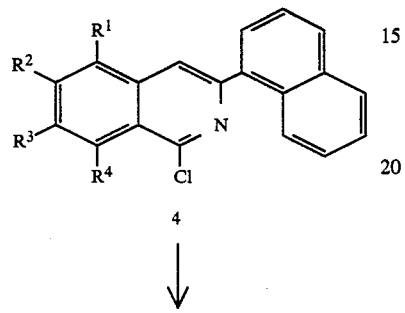

4

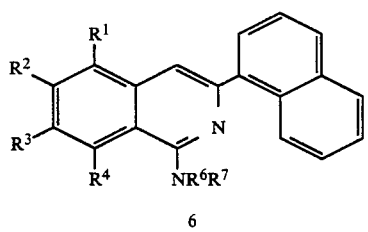

6

The compounds of Formula (I) wherein X is NH₂ can be prepared according to the route shown in Scheme 3. The 2-methylbenzonitrile (6) is metalated with potassium amide in liquid ammonia. The potassium salt reacts with 1-cyanonaphthalene to afford, after workup, the compounds of Formula (7). The compounds of Formula (7) may be elaborated to the compounds of Formula (5) by reactions such as the alkylation of (7) with appropri-ate alkyl halides or the like, or the reductive alkylation of (7) with an appropriate aldehyde.

Scheme 3

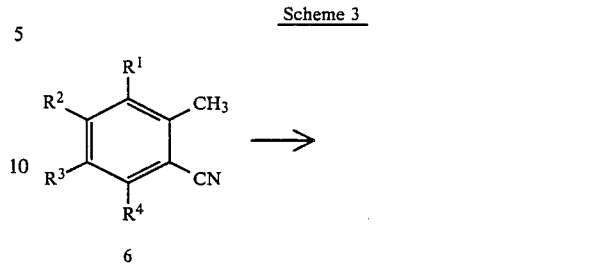

6

7

Scheme 4

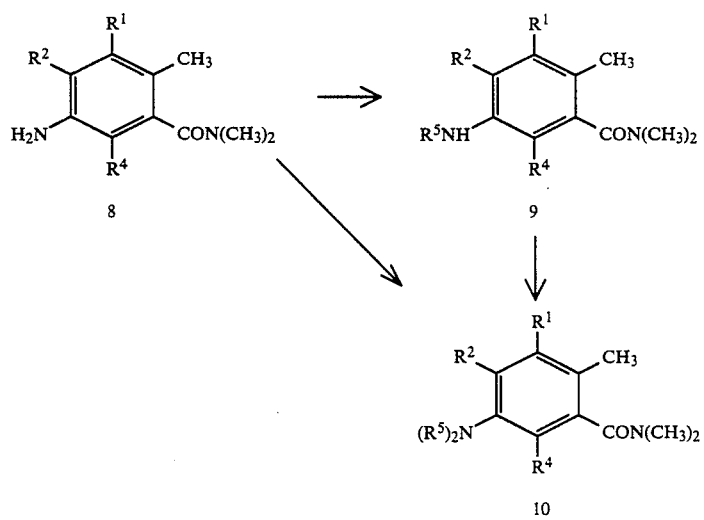

The compounds of Formula I wherein X is O, R³ is N(R⁵)₂, and the R⁵ substituents are identical can be prepared from the corresponding amides (2) as shown in Scheme 1. The compounds of Formula (2) wherein R³ is N(R⁵)₂ and the R⁵ substituents are identical are prepared as shown in Scheme 4. The 5-dialkylamino-N,N,2-trimethylbenzamide (10) is prepared directly by the reductive alkylation of 5-amino-N,N,2-trimethylbenzamide (8) with excess aldehyde with a reducing agent such as zinc chloride modified sodium cyanoborohydride in a solvent such as methanol as described by Kim et al. [J. Org. Chem. 50, 1927–1932 (1985)].

The compounds of Formula I wherein X is O, R³ is N(R⁵)₂ and the R⁵ substituents are not identical are also prepared from the corresponding amides (2) as shown in Scheme 1. The compounds of Formula (2) wherein R³ is N(R⁵)₂ and the R⁵ substituents are not identical are prepared as shown in Scheme 4. The 5-alkylamino-N,N,2-trimethylbenzamide (9) is prepared by the reductive alkylation of 5-amino-N,N,2-trimethylbenzamide (8) by the procedure described above with the exception that one equivalent of the appropriate aldehyde is used instead of an excess of the aldehyde. The 5-dialkylamino-N,N,2-trimethylbenzamide (10) wherein $R^3$ is $N(R^5)_2$ and the $R^5$ substituents are not identical are prepared by a reductive alkylation of (9) as described above with a different aldehyde. Although the compounds of Formula I wherein X is O, $R^3$ is $N(R^5)_2$ or $N^+(R^5)_3I^-$, and the $R^5$ substituents are not identical are not specifically exemplified, they are equivalent to the compounds which are exemplified.

The compounds of Formula I wherein X is O and $R^3$ is $^+N(R^5)_3I^-$ are prepared by the alkylation of the compounds of Formula (3b) where in $R^3$ is $N(R^5)_2$ with an appropriate alkyl iodide in accordance with well-known techniques of forming salts.

The preparation of pharmaceutically acceptable salts of the compounds of Formula (I) can be in accordance with well-known techniques of forming salts.

The compounds of this invention and their preparation can be further understood by the following examples, which do not constitute a limitation of the invention. In these examples, all temperatures are in degrees Centigrade. All melting points are uncorrected. All reactions were conducted in dry glassware under a nitrogen atmosphere. All commercial chemicals were used as received except as noted below. 1-Cyanonaphthalene was distilled under vacuum. Diisopropylamine was distilled from $CaH_2$ under nitrogen. Chromatography was performed with Merck silica gel 60 (230-400 mesh). The chromatography eluents are given as ratios by volume. Ether refers to diethyl ether, DMF refers to N,N,-dimethylformamide, EtOH refers to ethanol, THF refers to tetrahydrofuran, and LDA refers to lithium diisopropylamide. Peak positions for $^1H$ NMR spectra are reported as parts per million ($\delta$) downfield from the tetramethylsilane internal standard. Abbreviations for $^1H$ NMR spectra are as follows: s=singlet, d=doublet, and m=multiplet.

EXAMPLE 1

Preparation of 3-(1-Naphthalenyl)-1(2H)-isoquinolinone

Part A. A 2-L, three-necked, round-bottomed flask equipped with an addition funnel, reflux condenser, and a nitrogen sweep to an HCl gas scrubber was charged with 2-methylbenzoic acid (503 g, 3.69 mol). The apparatus was cooled in an ice bath, and thionyl chloride (750 mL, 10.3 mol) was added over a period of 15 minutes. After complete addition, the ice bath was removed and the reaction mixture was warmed to about 45° in order to completely dissolve the 2-methylbenzoic acid. The reaction mixture was then allowed to gradually cool with stirring to room temperature overnight. The excess thionyl chloride and the HCl and $SO_2$ reaction side-products were removed by vacuum distillation to afford 2-methylbenzoyl chloride as an oil, which was used without further purification. This material was transferred immediately into an addition funnel and added with mechanical stirring in 30-50 mL portions over a period of one hour to a commercial 40% dimethylamine solution (1500 mL, 13.35 mmol) which was maintained below 25° by periodic cooling with a dry ice-acetone bath. After complete addition the reaction mixture was stirred at room temperature for 1.5 hours. The reaction mixture was extracted with ether, and the combined organic extracts were washed with water, dried, and concentrated. The resulting oil was distilled under vacuum to afford N,N,2-trimethylbenzamide (409 g, 2.49 mol, 68% yield) as an oil: bp 88° (0.4 torr); IR(neat) 1650 cm$^{-1}$; $^1$H NMR(CDCl$_3$) $\delta$ 7.07-7.30 (m,4H), 3.11(s,3H), 2.81(s,3H), 2.27(s,3H). Anal. Calcd for C$_{10}$H$_{13}$NO: C,73.59; H,8.03; N,8.58. Found: C,73.66; H,8.18; N,8.42.

Part B. A solution of LDA in THF was prepared by the dropwise addition of 1.55M n-butyllithium in hexanes (130 mL, 202 mmol) to a solution of diisopropylamine (28.5 mL, 203 mmol) in THF (500 mL) at −78°. A solution of the product of Part A (30.00 g, 183.8 mmol) in THF (50 mL) was added dropwise at −78° to the LDA in THF solution, and the reaction mixture was stirred for one hour at −78°. A solution of 1-cyanonaphthalene (28.15 g, 183.8 mmol) in THF (50 mL) was then added dropwise to the reaction mixture at −78°, and after complete addition the reaction mixture was allowed to gradually warm to room temperature and stirred overnight. The reaction mixture was quenched with excess saturated aqueous NH$_4$Cl and then most of the THF was removed by distillation under nitrogen. The resulting precipitate was filtered, washed with water, dried, and recrystallized from DMF-EtOH to afford the title compound (41.6 g, 153.3 mmol, 83% yield) as a white solid. The mother liquor was concentrated and the residue was recrystallized from DMF-EtOH to afford a second crop (5.6 g, 20.6 mmol, 11% yield) as a white solid: mp 225°-226°; IR(CHCl$_3$) 1573 cm$^{-1}$; MS m/e 272(M$^+$+H); $^1$H NMR(DMF-d$^7$) $\delta$ 11.49(s,1H), 8.33(d,J=7.9 Hz,1H), 7.87-8.17(m,3H), 7.47-7.85(m,7), 6.72(s,1H). Anal. Calcd for C$_{19}$H$_{13}$NO: C,84.11; H,4.83; N,5.16. Found: C,83.90; H,4.70; N,5.12.

EXAMPLE 2

Preparation of 7-chloro-3-(1-naphthalenyl)-1(2H)-isoquinolinone

Part A. A 100-mL, three-necked, round-bottomed flask equipped with an addition funnel, reflux condenser, and a nitrogen sweep to an HCl gas scrubber was charged with 5-chloro-2-methylbenzoic acid (10.00 g, 58.62 mmol). The apparatus was cooled in an ice bath, and thionyl chloride (40 mL, 550 mmol) was added in one portion. The ice bath was removed and the reaction mixture was warmed to about 50° for about 45 minutes in order to completely dissolve the 5-chloro-2-methylbenzoic acid. The reaction mixture was allowed to gradually cool with stirring to room temperature overnight. The excess thionyl chloride and the HCl and SO$_2$ reaction side-products were removed by vacuum distillation. The residue was distilled under vacuum to afford 5-chloro-2-methylbenzoyl chloride as an oil: bp 65° (0.2 torr). This material was transferred immediately into an addition funnel and added dropwise with stirring to a commerical 40% dimethylamine solution (50 mL, 445 mmol) in water (150 mL). After complete addition, the reaction mixture was stirred at room temperature for 2 hours. The reaction mixture was extracted with ether, washed with water, dried, and concentrated. The resulting oil was distilled under vacuum to afford 5-chloro-N,N-2-trimethylbenzamide (10.40 g, 52.65 mmol, 90% yield) as an oil: bp 95°-101° (0.15 torr); IR(neat) 1650 cm$^{-1}$; $^1$H NMR(CDCl$_3$) $\delta$ 7.07-7.53(m,3H), 3.12(s,3H), 2.84(s,3H). Anal. Calcd for C$_9$H$_{12}$ClNO: C,60.76; N,6.12; Cl,17.94; N,7.12. Found: C,60.57; N,6.06; Cl,17.84; N,6.86.

Part B. A solution of LDA in THF was prepared by the dropwise addition of 1.55M n-butyllithium in hexanes (56 mL, 87 mmol) to a solution of diisopropylamine (12 mL, 36 mmol) in THF (700 mL) at −78°. A solution of the product of Part A (10.00 g, 50.6 mmol) in THF (50 mL) was added dropwise at −78° to the LDA in THF solution, and the reaction mixture was stirred for 3.75 hours at −78°. A solution of 1-cyanonaphthalene (7.75 g, 50.6 mmol) in THF (50 mL) was then added dropwise to the reaction mixture at −78°, and after complete addition the reaction was allowed to gradually warm with stirring to room temperature overnight. The reaction mixture was quenched with excess saturated aqueous $NH_4Cl$, and then most of the THF was removed by distillation under nitrogen. The resulting precipitate was filtered, washed with water, dried, and recrystallized from DMF-EtOH to afford the title compound (5.5 g, 18.0 mmol, 36% yield) as a solid. The mother liquor was concentrated and the residue was recrystallized from DMF-EtOH to afford a second crop (1.8 g, 5.9 mmol, 11% yield) as a solid: mp 260°–262°; MS m/e 305($M^+$), IR(KBr pellet) 1660 $cm^{-1}$; $^1$H NMR($CDCl_3$) δ 8.77(broad s,1H), 8.43(m,1H), 7.90–8.10(m,3H), 7.50–7.73(m,6H), 6.68(s,1H); HRMS m/e calcd for $C_{19}H_{12}ClNO$ ($M^+$) 305.0608, found 305.0601.

EXAMPLE 3

Preparation of 7-Methyl-3-(1-naphthalenyl)-1(2H)-isoquinolinone

Part A. A 500-mL, three-necked, round bottomed flask equipped with an addition funnel, reflux condenser, and a nitrogen sweep to an HCl gas scrubber was charged with 2,5-dimethylbenzoic acid (50.0 g, 332.9 mmol). The apparatus was cooled in an ice bath and thionyl chloride (125 mL, 1714 mmol) was added over a period of about 5 minutes. After complete addition, the ice bath was removed and the reaction mixture was warmed to about 50° in order to completely dissolve the 2,5-dimethylbenzoic acid. The reaction mixture was allowed to gradually cool with stirring to room temperature overnight. The excess thionyl chloride and the HCl and $SO_2$ reaction side-products were removed by vacuum distillation to afford 2,5-dimethylbenzoyl chloride as an oil, which was used without further purification. This material was transferred immediately to an addition funnel and added dropwise with stirring to a commercial 40% dimethylamine solution (188 mL, 1670 mmol) which was maintained between −5° and 5° by periodic immersion in a dry ice-acetone bath. After complete addition, the reaction mixture was stirred at room temperature for 1 hour. The reaction mixture was diluted with water and extracted with ether. The combined organic extracts were washed with water, dried, and concentrated. The resulting pale yellow oil was distilled under vacuum to afford N,N,2,5-tetramethylbenzamide (29.1 g, 164.2 mmol, 49% yield) as a clear, colorless oil: bp 100° (1.0 torr); IR($CHCl_3$) 1637 $cm^{-1}$; MS m/e 178($M^+$ +H); $^1$H NMR($CDCl_3$) δ 7.00–7.13(m,2H), 6.90–7.00(m,1H), 3.13(s,3H), 2.84(s,3H), 2.31(s,3H), 2.23(s,3H). Anal. Calcd for $C_{11}H_{15}NO$: C,74.54; H,8.53; N,7.90. Found: C,74.30; H,8.77; N,7.73.

Part B. A solution of LDA in THF was prepared by the dropwise addition of 1.55M n-butyllithium in hexanes (111 mL, 166 mmol) to a solution of diisopropylamine (22.6 mL, 161 mmol) in THF (750 mL) at −78°. A solution of the product of Part A (29.13 g, 164.3 mmol) in THF (50 mL) was added dropwise to the LDA in THF solution at −78° and the reaction mixture was stirred for 1 hour at −78°. A solution of 1-cyanonaphthalene (25.2 g, 164.5 mmol) in THF (50 mL) was then added dropwise to the reaction mixture at −78°, and the reaction mixture was stirred at −78° for 1 hour after complete addition and then allowed to gradually warm with stirring to room temperature overnight. The reaction mixture was quenched with excess saturated aqueous $NH_4Cl$, and then most of the THF was removed by distillation under nitrogen. The resulting precipitate was filtered, washed with water, dried, and recrystallized from hexane-ethyl acetate to afford the title compound (32.0 g, 112.1 mmol, 68% yield) as a solid: mp 221°–222°; MS m/e 286($M^+$ +H); IR($CHCl_3$) 1651 $cm^{-1}$; $^1$H NMR($CDCl_3$) δ 8.70(s,1H), 8.23(s,1H), 7.83–8.13(m,3H), 7.40–7.73(m,6H), 6.67(s,1H), 2.53(s,3H). Anal. Calcd for $C_{20}H_{15}NO$: C,84.19; H,5.30; N,4.91. Found: C,83.93; H,5.03; N,4.79.

EXAMPLE 4

Preparation of 7-(Dimethylamino)-3-(1-naphthalenyl)-1(2H)-isoquinolinone hydrochloride Part A. A 1-L flask equipped with a reflux condenser and a nitrogen sweep to an HCl gas scrubber was charged with 2-methyl-5-nitrobenzoic acid (200 g, 1.10 mol). The reaction vessel was cooled in an ice bath and thionyl chloride (307 mL, 4.20 mol) was added in one portion. The ice bath was removed, and the reaction mixture was refluxed overnight. The excess thionyl chloride and the $SO_2$ and HCl reaction side-products were removed by vacuum distillation to afford 2-methyl-5-nitrobenzoyl chloride as a solid residue, which was used without further purification. This material was immediately dissolved in methylene chloride (100 mL) and added dropwise with stirring to a commercial 40% dimethylamine solution (500 mL, 4.45 mol) which was maintained at 0° to 12° by periodic immersion in a dry ice-acetone bath. After complete addition, the reaction mixture was stirred for 30 minutes at room temperature. The reaction mixture was diluted with water and extracted with methylene chloride. The combined organic extracts were washed with water, dried, and concentrated. The resulting material was distilled under vacuum to afford 5-nitro-N,N,2-trimethylbenzamide (189.9 g, 0.91 mol, 83% yield) as a solid: mp 98°–99°; bp 156°–170° (0.5 torr); MS m/e 209($M^+$ +H); $^1$H NMR($CDCl_3$) δ 8.00–8.17(m,2H), 7.40(d,J=8 Hz,1H), 3.17(s,3H), 2.88(s,3H), 2.41(s,3H). Anal. Calcd for $C_{10}H_{12}N_2O_3$: C,57.69; H,5.81; N,13.45. Found: C,57.72; H,5.84; N,13.49.

Part B. A solution of the product of Part A, (20.0 g, 96.1 mmol) in methanol (100 mL) was hydrogenated overnight under 50 psi $H_2$ with 5% Pd on carbon (0.5 g, 2.5 wt %) as a catalyst in a Parr hydrogenation apparatus. The reaction mixture was filtered through celite, and the filter cake was washed with methanol. The combined methanol portions were concentrated and the residue dried under vacuum to afford 5-amino-N,N,2-trimethylbenzamide (17.0 g, 95.4 mmol, 99% yield) as off-white crystals: mp 114°–115°; MS m/e 179($M^+$ +H), IR($CHCl_3$) 3372, 1630 $cm^{-1}$; $^1$H NMR($CDCl_3$) δ 6.96(d,J=8 Hz,1H), 6.58(m,1H), 6.49(d,J=2 Hz,1H), 3.67(s,2H), 3.10(s,3H), 2.83(s,3H), 2.14(s,3H). Anal. Calcd for $C_{10}H_{14}N_2O$: C,67.39; H,7.92; N,15.72. Found: C,67.16, H,8.20; N,15.78.

Part C. A zinc-modified borohydride reducing agent was prepared by the cautious portionwise addition of ZnCl$_2$ (7.6 g, 55.6 mmol) to a solution of NaBH$_3$CN (7.05 g, 112.2 mmol) in methanol (100 mL) at 0°. This reagent, at 0° C., was added dropwise to a solution of the product of Part B (10.0 g, 56.1 mmol) in a mixture of 37% formaldehyde (15 mL, 185 mmol) and methanol (100 mL) at 0°. After complete addition, the reaction mixture was warmed to room temperature and stirred overnight. The reaction mixture was quenched with 1.0N NaOH (200 mL) and the methanol was removed with a rotary evaporator. The residue was extracted with ethyl acetate, and the combined organic extracts were washed with water, dried, and concentrated. The residue was distilled under vacuum to afford 5-(dimethylamino)-N,N,2-trimethylbenzamide (10.62 g, 51.5 mmol, 92% yield) as an oil: IR(CHCl$_3$) 1635 cm$^{-1}$; $^1$H NMR(CDCl$_3$) δ 6.93–7.10(m,1H), 6.67(m,1H), 6.50(m,1H), 3.12(s,3H), 2.90(s,6H), 2.84(s,3H), 2.15(s,3H). HRMS m/e calcd for C$_{12}$H$_{18}$N$_2$O (M$^+$) 206.1420, Found 206.1419.

Part D. A solution of LDA in THF was prepared by the dropwise addition of 1.6M n-butyllithium in hexanes (17 mL, 27 mmol) to a solution of diisopropylamine (4.0 mL, 28.5 mmol) in THF (50 mL) at −78°. A solution of the product of Part C (5.00 g, 24.2 mmol) in THF (15 mL) was added dropwise to the LDA solution at −78° and the reaction mixture was stirred for one hour at −78°. A solution of 1-cyanonaphthalene (3.70 g, 24.2 mmol) in THF (15 mL) was added dropwise to the reaction mixture at −78°, and the reaction mixture was stirred at −78° for 1 hour after complete addition and then allowed to gradually warm with stirring to room temperature for 2 hours. The reaction mixture was quenched with excess saturated aqueous NH$_4$Cl. The layers were separated and the aqueous phase was extracted with ether. The combined organic extracts were washed with saturated NaCl, dried, and concentrated. The residue was recrystallized from ethyl acetate to afford 7-(dimethylamino)-3-(1-naphthalenyl)-1(2H)-isoquinolinone (1.84 g, 5.85 mmol, 24% yield) as a solid. The mother liquor was concentrated and the residue was recrystallized from 6:4:0.5 hexane-ethyl acetate-methanol to afford a second crop (1.41 g, 4.48 mmol, 19% yield) as a solid: mp 205°–206°; IR(CHCl$_3$) 1650 cm$^{-1}$; HRMS m/e calcd for C$_{21}$H$_{18}$N$_2$O (M$^+$) 314.1419, found 314.1426; $^1$H NMR(CDCl$_3$) δ 8.72(s,1H), 8.00–8.17(m,1H), 7.83–8.00(m,2H), 7.38–7.70(m,6H), 7.10–7.29(m,1H), 6.63(s,1H), 3.10(s,6H). Anal. Calcd for C$_{21}$H$_{18}$N$_2$O: C,80.23; H,5.77; N,8.91. Found: C,79.88; H,5.58; N,8.71.

Part E. The product of Part D (0.4 g, 1.3 mmol) was warmed in concentrated hydrochloric acid (25 mL) on a steam bath until there was complete solution. The reaction mixture was then allowed to cool gradually to room temperature and then refrigerated at 0°. The precipitate was filtered and dried to afford the title compound (0.4 g, 1.1 mmol, 88% yield) as a solid: mp 244°.

EXAMPLE 5

Preparation of 1,2-Dihydro-N,N,N-trimethyl-2-(1-naphthalenyl)-1-oxoisoquinolinaminium iodide A solution of the product of Example 4, Part D, 7-(dimethylamino)-3-(1-naphthalenyl)-1(2H)-isoquinolinone (0.50 g, 1.59 mmol) in methyl iodide (10 mL) was refluxed overnight. The reaction mixture was concentrated and the residue was dried to afford the title compound (0.70 g, 1.53 mmol, 96% yield) as a solid: mp 207°; $^1$H NMR(DMSO) δ 12.00(s,1H), 8.60–8.77(m,1H), 8.23–8.43(m,1H), 7.77–8.10(m,4H), 7.43–7.73(m,4H), 6.73(s,1H), 3.83(s,9H).

The compounds of Examples 1, 2, 3, 4, and 5, and other compounds of Formula I wherein X is O, which have been prepared or which may be prepared using the procedures of Examples 1, 2, 3, 4 and 5 are listed in Table 1.

TABLE 1

| Ex. | R$^1$ | R$^2$ | R$^3$ | R$^4$ | mp (°) |
|---|---|---|---|---|---|
| 1 | H | H | H | H | 225–226 |
| 2 | H | H | Cl | H | 260–262 |
| 3 | H | H | Me | H | 221–222 |
| 4 | H | H | NMe$_2$.HCl | H | 244 |
| 5 | H | H | $^+$NMe$_3$I$^-$ | H | 207 |
| 6 | Cl | H | H | H | |
| 7 | Me | H | H | H | 244–245 |
| 8 | H | Cl | H | H | |
| 9 | H | Me | H | H | 241–242 |
| 10 | H | H | NEt$_2$.HCl | H | |
| 11 | H | H | N(n-Pr)$_2$.HCl | H | |
| 12 | H | H | $^+$NEt$_3$I$^-$ | H | |
| 13 | H | H | $^+$N(n-Pr)$_3$I$^-$ | H | |
| 14 | H | H | H | Cl | |
| 15 | H | H | H | Me | 235–236 |

Representative compounds of Formula I wherein X is NR$^6$R$^7$ are listed in Table 2. Compounds of Table 2 designated Examples 20, 21, 31, and 40 were prepared as described in the following Examples 20, 21, 31 and 40. Other compounds of Table 2 were prepared or could be prepared using the same or similar synthetic methods.

EXAMPLE 20

Preparation of 6-Methyl-3-(1-naphthalenyl)-1-isoquinolineamine

A 250-mL, three-necked, round-bottomed flask equipped with a dry ice-acetone cooled reflux condenser, addition funnel, and a gas inlet was charged with liquid ammonia (175 mL). Iron (III) nitrate nonahydrate (0.23 g, 0.57 mmol) was added to the liquid NH$_3$ in one portion as a solid, and then potassium metal (4.2 g, 107.4 mmol) was added cautiously in small portions. A solution of 2,4-dimethylbenzonitrile (7.0 g, 53.4 mmol) in THF (20 mL) was added to the reaction mixture dropwise over a period of 5 minutes, the reaction was stirred for 15 minutes, a solution of 1-cyanonaphthalene (12.6 g, 79.8 mmol) in THF (30 mL) was then added dropwise over a period of 10 minutes, and the reaction mixture was allowed to stir overnight as the liquid ammonia gradually evaporated. The crude reaction mixture was cautiously poured into excess ice water. The layers were separated, and the aqueous phase was extracted with methylene chloride. The combined organic extracts were dried and concentrated. The residue was purified by flash chromatography with 2:1 hexane-ethyl acetate, and the crude product was recrystallized from 2:1 hexane-ethyl acetate to afford the title compound (3.82 g, 13.4 mmol, 24% yield) as a solid: mp 170°; IR(CHCl$_3$) 3512, 3409 cm$^{-1}$; MS m/e 285(M$^+$+H); $^1$H NMR(CDCl$_3$) δ 8.13–8.23(m,1H), 7.80–7.97(m,2H), 7.62–7.78(m,2H), 7.37–7.61(m,1H), 7.27–7.36(m,1H), 7.17–7.26(m,1H), 5.28(s,2H), 2.51(s,3H); HRMS m/e calcd for C$_{20}$H$_{16}$N$_2$ (M$^+$) 284.1315, Found 284.1305. Anal. Calcd for C$_{20}$H$_{16}$N$_2$: C,84.48; H,5.67; N,9.85. Found: C,84.39; H,5.63; N,9.57.

EXAMPLE 21

Preparation of
7-Chloro-3-(1-naphthalenyl)-1-isoquinolineamine

A 500-mL, three-necked, round-bottomed flask equipped with a dry ice-acetone cooled reflux condenser, addition funnel, and a gas inlet was charged with liquid ammonia (150 mL). Iron (III) nitrate nonahydrate (spatula end) was added in one portion as a solid, and then potassium metal (5.16 g, 132.0 mmol) was added cautiously in small portions. A solution of 5-chloro-2-methylbenzonitrile (10.00 g, 65.96 mmol) in THF (30 mL) was added dropwise over 5 minutes, the reaction mixture was stirred for 5 minutes, a solution of 1-cyanonaphthalene (15.16 g, 98.97 mmol) in THF was added dropwise over 5 minutes, and the reaction mixture was allowed to stir overnight as the liquid ammonia gradually evaporated. The crude reaction mixture was cautiously poured into saturated aqueous NH$_4$Cl, and the aqueous phase was extracted with methylene chloride. The combined organic extracts were dried and concentrated. The residue was purified by flash chromatography with 2:1 hexane-ethyl acetate, and the crude product was recrystallized from 2:1 hexane-ethyl acetate to afford the title compound (2.88 g, 9.45 mmol, 14% yield) as yellow crystals: mp 180°–181°; IR(CHCl$_3$) 3513, 3409 cm$^{-1}$; MS m/e 305 (M$^+$+H NMR(CDCl$_3$) δ 8.00–8.17(m,1H), 7.83–8.00(m,2H), 7.80(s,1H), 7.33–7.79(m,6H), 7.25(s,1H), 5.35(s,2H). Anal. Calcd for C$_{19}$H$_{13}$ClN$_2$: C,74.88; H,4.30; Cl,11.83; N,9.19. Found: C,74.77; H,4.09; Cl,11.87; N,8.81.

EXAMPLE 31

Preparation of
7-Methyl-1-(4-methyl-1-piperazinyl)-3-(1-naphthalenyl)-isoquinoline Part A. A 500-mL, round-bottomed flask equipped for a nitrogen sweep to an HCl gas scrubber was charged with the product of Example 3, Part B (25.0 g, 87.6 mmol) and phosphorous oxychloride (250 mL) and stirred at 50° overnight. The phosphorous oxychloride was removed by vacuum distillation. The pot residue was cooled to room temperature and crystallized by the addition of ethyl acetate. The crude precipitate was recrystallized from ethyl acetate and then recrystallized from 3:1 hexane-ethyl acetate to afford 1-chloro-7-methyl-3-(1-naphthalenyl)-isoquinoline (21.0 g, 69.1 mmol, 79% yield) as a solid: mp 93°; IR(CHCl$_3$) 1585 cm$^{-1}$; MS m/e 304(M$^+$+H); HRMS m/e calcd for C$_{20}$H$_{14}$ClN (M$^{30}$) 303.0814, Found 303.0811; $^1$H NMR(CDCl$_3$) δ 8.29(s,1H), 7.80–8.10(m,6H), 7.70–7.79(m,1H), 7.43–7.69(m,3H), 2.70(s,3H). Anal. Calcd for C$_{20}$H$_{14}$ClN: C,79.07; H,4.65; Cl,11.67; N,4.61. Found: C,79.25; H,4.51; Cl,11.80; N,4.51.

Part B. A mixture of the product of Part A (2.0 g, 6.58 mmol), N-methylpiperazine (1.5 mL, 13.5 mmol), and potassium carbonate (2.75 g, 19.9 mmol) in DMF (5 mL) was refluxed overnight. The reaction mixture was cooled to room temperature, diluted with water, and extracted with methylene chloride. The combined organic extracts were washed with water, dried, and concentrated. The residue was purified by flash chromatography with 1:1 hexane-ethyl acetate to afford the title compound (2.2 g, 6.0 mmol, 91% yield) as a yellow powder: mp 150°; IR(CHCl$_3$) 3052, 3011 cm$^{-1}$; MS m/e 368 (M$^+$+H) $^1$H NMR(CDCl$_3$) δ 8.27–8.43(m,1H), 7.80–8.00(m,3H), 7.63–7.80(m,2H), 7.37–7.61(m,5H), 3.40–3.67(m,4H), 2.63–2.83(m,4H), 2.57(s,3H), 2.41(s,3H).

EXAMPLE 40

Preparation of
N,N,N'-Trimethyl-N'-(7-methyl-3-(1-naphthalenyl)-1-isoquinolinyl)-1,2-ethanediamine A mixture of the product of Example 31, Part A, 1-chloro-7-methyl-3-(1-naphthalenyl)-isoquinoline (2.00 g, 6.58 mmol), N,N,N'-trimethylethanediamine (1.7 mL, 13.4 mmol), and potassium carbonate (2.75 g, 19.9 mmol) in DMF (5 mL) was refluxed overnight. The reaction mixture was cooled to room temperature, diluted with water, and extracted with methylene chloride. The combined organic extracts were washed with water, dried, and concentrated. The residue was purified by flash chromatography with 1:1 hexane-ethyl acetate to afford the title compound (2.08 g, 5.63 mmol, 86% yield) as an oil: IR(CHCl$_3$) 3052, 1591 cm$^{-1}$; MS m/e 370(M$^+$+H); $^1$H NMR(CDCl$_3$) δ 8.23–8.37(m,1H), 8.03(s,1H), 7.80–7.97(m,2H), 7.63–7.79(m,2H), 7.33–7.62(m,5H), 3.62(t,J=7 Hz,2H), 3.13(s,3H), 2.80(t,J=7 Hz,2H), 2.60(s,3H), 2.30(s,6H).

TABLE 2

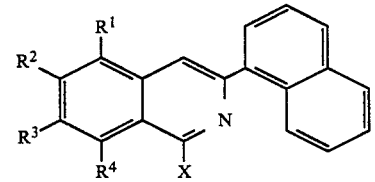

| Ex. | R$^1$ | R$^2$ | R$^3$ | R$^4$ | X | mp (°C.) |
|---|---|---|---|---|---|---|
| 16 | H | H | H | H | NH$_2$ | 104–106 |
| 17 | Cl | H | H | H | NH$_2$ | |
| 18 | Me | H | H | H | NH$_2$ | 172–173 |
| 19 | H | Cl | H | H | NH$_2$ | 176 |
| 20 | H | Me | H | H | NH$_2$ | 170 |
| 21 | H | H | Cl | H | NH$_2$ | 180–181 |
| 22 | H | H | Me | H | NH$_2$ | 154–155 |
| 23 | H | H | H | Cl | NH$_2$ | 165 |
| 24 | H | H | H | Me | NH$_2$ | 201 |
| 25 | H | H | H | H | /–\ N  NMe \–/ | |
| 26 | Cl | H | H | H | /–\ N  NMe.HCl \–/ | |
| 27 | Me | H | H | H | /–\ N  NMe \–/ | |

TABLE 2-continued

*[Structure: substituted isoquinoline with R¹, R², R³, R⁴ on benzene ring, =CH-naphthyl group, and N-X group]*

| Ex. | R¹ | R² | R³ | R⁴ | X | mp (°C.) |
|---|---|---|---|---|---|---|
| 28 | H | Cl | H | H | N-piperazinyl-NMe | |
| 29 | H | Me | H | H | N-piperazinyl-NMe·HCl | |
| 30 | H | H | Cl | H | N-piperazinyl-NMe | |
| 31 | H | H | Me | H | N-piperazinyl-NMe | 150 |
| 32 | H | H | H | Cl | N-piperazinyl-NMe·HCl | |
| 33 | H | H | H | Me | N-piperazinyl-NMe | |
| 34 | H | H | H | H | NMe(CH₂)₂NMe₂ | |
| 35 | Cl | H | H | H | NMe(CH₂)₂NMe₂ | |
| 36 | Me | H | H | H | NMe(CH₂)₂NMe₂·HCl | |
| 37 | H | Cl | H | H | NMe(CH₂)₂NMe₂ | |
| 38 | H | Me | H | H | NMe(CH₂)₂NMe₂ | |
| 39 | H | H | Cl | H | NMe(CH₂)₂NMe₂·HCl | |
| 40 | H | H | Me | H | NMe(CH₂)₂NMe₂ | Oil |
| 41 | H | H | H | Cl | NMe(CH₂)₂NMe₂ | |
| 42 | H | H | H | Me | NMe(CH₂)₂NMe₂·HCl | |

UTILITY

Results of the various biological tests described below establish that the compounds of this invention have the property of inhibiting the growth of transplanted mouse tumors in mice and also inhibiting the growth of human tumors implanted in mice.

The efficacy of the compounds of this invention against transplanted mouse tumors was evaluated in test systems which are used by the National Cancer Institute for the detection and assessment of anticancer activity. Most clinically effective drugs exhibit activity in these tests and the tests have a good record of predicting clinical efficacy [Goldin, A., Venditti, J. M., MacDonald, J. S., Muggia, F. M., Henney, J. E. and V. T. Devita, Jr., *Europ. J. Cancer*, 17, 129–142, (1981); Venditti, J. M., *Seminars in Oncology*, 8(4) (1981); Goldin, A. and J. M. Venditti in *Recent Results in Cancer Research*, 70, S. K. Carter and Y. Sakurai, Eds., Springer-Verlag, Berlin/Heidelberg, 1980].

L1210 MURINE LEUKEMIA TEST

The L1210 tumor line originated in 1948 as a lymphocytic leukemia in a female DBA/2 mouse after the skin was treated with 0.2% 20-methylcholanthrene in ethyl ether. The tumor line is maintained by serial passage in female DBA/2 mice. On day 0, female CDF₁ mice weighing 18–22 g are inoculated with $1 \times 10^5$ L1210 leukemia cells harvested from the ascites of DBA/2 mice. The mice are randomized into groups of six each and the test compounds and vehicle control are administered intraperitoneally once daily for nine consecutive days beginning on day 1. A $\geq 20\%$ decrease in body weight on day 5 is considered an indication of toxicity. The acceptable control mean survival time is 8–11 days. Results are expressed as a percentage of the mean survival time of the vehicle-treated control group according to the formula:

$$\% T/C = \frac{\text{Mean survival time of treated}}{\text{Mean survival time of control}} \times 100\%.$$

Mice which survive for 30 days are considered cured and are not included in the calculation of the mean survival time. The NCI criteria for activity are used. A compound is considered to have moderate activity against L1210 leukemia if it has a % T/C $\geq 125\%$, and it is considered to have good activity if it has a % T/C $\geq 150\%$.

The results of tests with the compounds of this invention are shown in Table 3. The data indicate that the compounds of this invention are effective against the L1210 leukemia in mice. Activity against L1210 leukemia is considered predictive of efficacy in treating mammalian lymphocytic leukemia.

TABLE 3

| Ex. | L1210 Leukemia % T/C (dose: mg/kg) |
|---|---|
| 1 | 148 (100) |
| 3 | 133 (200) |
| 4 | 156 (6) |

P388 MURINE LEUKEMIA TEST

The P388 tumor line originated in 1955 as a lymphocytic leukemia in a female DBA/2 mouse after the skin was painted with 3-methylcholanthrene. The tumor line is maintained by serial passage in female DBA/2 mice. On day 0, female CDF₁ mice weighing 18–22 g are inoculated intraperitoneally with $1 \times 10^6$ P388 leukemia cells harvested from the ascites of DBA/2 mice. The mice are randomized into groups of six each and the test compounds and vehicle control are administered intraperitoneally once daily for nine consecutive days beginning day 1. A decrease in body weight on day 5 that is $\geq 20\%$ is considered an indication of toxicity. The acceptable control mean survival time is 9–14 days. Results are expressed as a percentage of the mean survival time of the vehicle-treated control group according to the formula:

$$\% T/C = \frac{\text{Mean survival time of treated}}{\text{Mean survival time of control}} \times 100\%.$$

Mice which survive for 30 days are considered cured and are not included in the calculation of the mean survival time. The NCI criteria for activity are used. A compound is considered to have moderate activity against P388 leukemia if it has a % T/C $\geq 125\%$, and it is considered to have good activity if it has a % T/C $\geq 150\%$.

The results of tests with the compounds of this invention are shown in Table 4. The data indicate that the compounds of this invention are effective against the P388 leukemia in mice. Activity against P388 leukemia is considered predictive of efficacy in treating mammalian lymphocytic leukemia.

TABLE 4

| Ex. | P388 Leukemia % T/C (dose: mg/kg) |
|---|---|
| 1 | 161 (200) |
| 2 | 138 (100) |
| 3 | 152 (100) |

B16 MURINE MELANOMA TEST

The B16 tumor line arose spontaneously in 1954 on the skin at the base of the ear of a C57BL mouse. The tumor line is maintained by serial passage in female C57BL mice. On day 0, female B6C3F1 mice are inoculated intraperitoneally with 0.5 mL of a 10% tumor brei. This brei is prepared by homogenizing fresh B16 tumors, grown subcutaneously in C57BL mice, in cold physiological saline. Mice are randomized in groups of ten each, with 20 animals being in the control group. The test compounds and vehicle control are administered intraperitoneally once daily for nine consecutive days beginning on day 1. A $\geq 20\%$ decrease in body weight on day 5 is considered an indication of toxicity. The acceptable mean control survival time is 14-22 days. Results are expressed as a percentage of the mean survival time of the vehicle-treated control group according to the formula:

$$\% \ T/C = \frac{\text{Mean survival time of treated}}{\text{Mean survival time of control}} \times 100\%.$$

Mice which survive 90 days are considered cured and are not included in the calculation of the mean survival time. The NCI criteria for activity are used. A compound is considered to have moderate activity against B16 melanoma if it has a % T/C $\geq 125\%$, and it is considered to have good activity if it has a % T/C $\geq 150\%$.

The results of tests with compounds of this invention are shown in Table 5. The data indicate that the compounds of this invention are effective against the B16 melanoma in mice.

TABLE 5

| Ex. | B16 Melanoma % T/C (dose: mg/kg) |
|---|---|
| 3 | 149 (100) |
| 20 | 130 (6) |
| 21 | 138 (100) |
| 31 | 133 (6) |
| 40 | 135 (0.75) |

LOX HUMAN AMELANOTIC MELANOMA XENOGRAFT TEST

The LOX human amelanotic melanoma tumor line was obtained from Dr. Oystein Fodstad, Department of Biochemistry, Norwegian Radium Hospital, Oslo, Norway. The line is maintained by serial passage in athymic NCR-NU mice. On day 0, athymic nude mice, all of one sex weighing a minimum of 18 g for males and 17 g for females, are inoculated intraperitoneally with $1 \times 10^6$ LOX melanoma cells harvested from the ascites of athymic mice. The mice are randomized into groups of six each and the test compounds and vehicle control are administered intraperitoneally every fourth day beginning day 1 for a total of three injections. Animals are evaluated for toxicity on day 10. A decrease in body weight $\geq 20\%$ is considered an indication of toxicity. The acceptable control median survival time is 17-24 days. Results are expressed as a percentage of the median survival time of the vehicle-treated control group according to the formula:

$$\% \ T/C = \frac{\text{Mean survival time of treated}}{\text{Mean survival time of control}} \times 100\%.$$

The NCI criteria for activity are used. A compound is considered to have moderate activity against LOX melanoma if it has a % T/C $\geq 140\%$, and it is considered to have good activity if it has a % T/C $\geq 200\%$.

The results of tests with the compounds of this invention are shown in Table 6. The data indicate that the compounds of this invention are effective against the LOX human amelanotic melanoma xenograft in mice.

TABLE 6

| Ex. | LOX Melanoma % T/C (dose: mg/kg) | Cures[a] |
|---|---|---|
| 1 | 168 (400) | 1/6 |
| 3 | 271 (240) | 2/6 |

Notes: (a) Cures = number of survivors/total at 60 days.

IN VITRO RPMI-7272 HUMAN MELANOMA TEST

The compounds of this invention were also tested for their ability to inhibit the growth of human melanoma RPMI-7272 cells in vitro.

Human melanoma RPMI-7272 cells (Quinn et al. [J. Natl. Cancer Inst. 59, 301-305 (1977)]) were propagated in RPMI-1640 medium supplemented with 10 mM Tricine (pH 7.8), 10 mM HEPES (pH 7.3), 0.075% sodium bicarbonate, and 10% (vol/vol) heat-inactivated (56° C., 30 minutes) fetal bovine serum in a 95% air:5% $CO_2$ humidified atmosphere. Cells were seeded at $3 \times 10^5$ per 35 mm plate to initiate growth inhibition studies. Cultures to receive growth medium only (control cultures) were set up in quadruplicate; cultures to receive varying concentrations of compounds were set up at one dish per dose of compound. Twenty-four hours post-seeding, duplicate control cell cultures were trypsinized and cells were counted using a Coulter Counter (day 1 control counts). At this time, varying concentrations of test compounds, from 100 to 0.00001 μg/mL were added to cultures and growth medium only was added to control cultures. Seventy-two hours after the addition of compound, cells were trypsinized and counted. The numbers of cell population doublings (day 4) in the presence or absence of compound were calculated. The $ID_{50}$ represents the dose of compound (in μg/mL) required to inhibit the number of cell doublings by 50%. A compound is considered to have in vitro activity against RPMI-7272 melanoma if it has an $ID_{50} \leq 1$ μg/mL. The number of population doublings of control cultures during 72 hours was between 3 and 4. Compounds were dissolved at 10-25 mg/mL in dimethylsulfoxide. Dilutions to 1 mg/mL in complete growth medium were made, followed by stock preparations of 100 and 30 μg/mL in complete growth medium. Serial ten-fold dilutions in complete medium were formulated from the 100 and 30 μg/mL stocks, respectively, and added to cultures.

The results of tests with the compounds of this invention are shown in Table 7. The data indicate that the compounds of this invention are potent inhibitors of RPMI-7272 human melanoma cell growth in vitro.

The efficacy of the compounds of the invention in the foregoing battery of solid tumor tests suggests that they may have anti-tumor activity against solid tumors in mammals.

TABLE 7

| Ex. | RPMI-7272 Melanoma $ID_{50}$ (μg/mL) |
|---|---|
| 2 | 0.005 |
| 3 | 0.0072 |
| 4 | 0.001 |
| 5 | 0.055 |
| 7 | 0.29 |
| 9 | 0.0016 |
| 15 | 0.53 |
| 16 | 0.22 |
| 18 | 0.95 |
| 19 | 0.055 |
| 20 | 0.00077 |
| 21 | 0.0094 |
| 22 | 0.0016 |
| 23 | 0.07 |
| 24 | 0.05 |

DOSAGE FORMS

The antitumor compound (active ingredients) of this invention can be administered to inhibit tumors by any means that delivers the active ingredient to the agent's site of action in the body of a mammal. They can be administered by a variety of known means available for use in conjunction with pharmaceuticals, either as individual therapeutic active ingredients or in a combination of therapeutic active ingredients. Antitumor compounds are frequently administered as part of a multiple drug protocol. These compounds can be administered alone, but are generally administered with a pharmaceutical carrier selected on the basis of the chosen route of administration and standard pharmaceutical practice. A variety of therapeutic regimens have been developed to maximize efficacy and minimize toxicity.

The dosage administered will be a tumor-inhibiting amount of active ingredient and will, of course, vary depending upon known factors such as the pharmacodynamic and pharmacokinetic characteristics of the particular active ingredient, and its mode and route of administration; age, health, and weight of the recipient; nature and extent of the disease; kind of concurrent treatment, frequency of treatment, and the effect desired. Usually a daily dosage of active ingredient can be about 5 to 400 milligrams per kilogram of body weight. Ordinarily, 10 to 200, and preferably 10 to 50, milligrams per kilogram per day given as a single dose or in divided doses 2 to 4 times a day, or in sustained release form or IV infusion, is effective to obtain desired results.

Dosage forms (compositions) suitable for internal administration ordinarily contain from about 1.0 milligram to about 500 milligrams of active ingredient per unit. In these pharmaceutical compositions, the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, including intravenous infusions. There are many parenteral routes of administration, including intravenous, subcutaneous, intramuscular, and intrathecal. The desired route of administration will affect the nature of the formulation required.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water for injection, a suitable oil, sodium chloride injection, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, osmotic and buffer substances. Antioxidizing agents such as sodium bisulfite, sodium sulfite, or ascorbic acid either alone or combined may be suitable stabilizing agents. Also used are citric acid and its salts and sodium EDTA. In addition, parenteral solutions can contain preservatives, such as benzalkonium chloride, methyl- or propyl-paraben, and chlorbutanol. Whether or not the vehicle itself must be sterile depends on whether the formulation as a whole will be sterilized prior to administration. For example, Sterile Water for Injection, USP must meet the USP Sterility Test, but Water for Injection need not since it is to be used in a product which will be sterilized.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay or control absorption.

INJECTABLE

A parenteral composition suitable for administration by injection is prepared by stirring 1.5% by weight of active ingredient in 10% by volume propylene glycol and Water for Injection, USP. The solution is made isotonic with sodium chloride and sterilized.

SUSPENSION

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

I claim:

1. A compound of Formula (I)

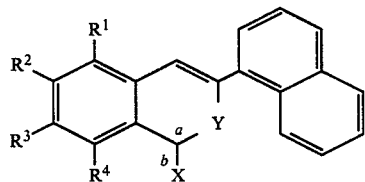

wherein
$R^1$ is H, $CH_3$, or Cl;
$R^2$ is H, $CH_3$, or Cl;
$R^3$ is $R^5$, Cl, $N(R^5)_2$, or $N^+(R^5)_3 I^-$ provided that, if X is $NR^6R^7$, $R^3$ is not $N(R^5)_2$ or $N^+(R^5)_3 I^-$;
$R^4$ is H, $CH_3$, or Cl;
$R^5$ is H, or $C_1$ to $C_3$ alkyl;
X is O, or $NR^6R^7$; provided that, if X is O, a is a single bond, b is a double bond, and Y is NH, and, if X is $NR^6R^7$, a is a double bond, b is a single bond, and Y is N;
$R^6$ and $R^7$ independently are $R^5$, $(CH_2)_n N(R^5)_2$ where n is 2 to 8, or $R^6$ and $R^7$ taken together represent $(CH_2CH_2)_2 NR^5$;
and pharmaceutically acceptable salts thereof.

2. A compound of claim 1, wherein $R^1$ is H; $R^2$ is H or $CH_3$; and $R^4$ is H.

3. The compound of claim 1 which is 3-(1-naphthalenyl)-1(2H)-isoquinolinone.

4. The compound of claim 1 which is 7-chloro-3-(1-naphthalenyl)-1(2H)-isoquinolinone.

5. The compound of claim 1 which is 7-methyl-3-(1-naphthalenyl)-1(2H)-isoquinolinone.

6. The compound of claim 1 which is 7-(dimethylamino)-3-(1-naphthalenyl)-1-(2H)-isoquinolinone hydrochloride.

7. The compound of claim 1 which is 6-methyl-3-(1-naphthalenyl)-1-isoquinolineamine.

8. The compound of claim 1 which is 7-chloro-3-(1-naphthalenyl)-1-isoquinolineamine.

9. The compound of claim 1 which is 7-methyl-1-(4-methyl-1-piperazinyl)-3-(1-naphthalenyl)-isoquinoline.

10. The compound of claim 1 which is N,N,N'-trimethyl-N'-(7-methyl-3-(1-naphthalenyl)-1-isoquinolinyl)-1,2-ethanediamine.

11. A pharmaceutical composition consisting essentially of a therapeutically effective amount of a compound of claim 1 and a pharmaceutically acceptable carrier.

12. A pharmaceutical composition consisting essentially of a therapeutically effective amount of a compound of claim 2 and a pharmaceutically acceptable carrier.

13. A pharmaceutical composition consisting essentially of a therapeutically effective amount of a compound of claim 3 and a pharmaceutically acceptable carrier.

14. A pharmaceutical composition consisting essentially of a therapeutically effective amount of a compound of claim 4 and a pharmaceutically acceptable carrier.

15. A pharmaceutical composition consisting essentially of a therapeutically effective amount of a compound of claim 5 and a pharmaceutically acceptable carrier.

16. A pharmaceutical composition consisting essentially of a therapeutically effective amount of a compound of claim 6 and a pharmaceutically acceptable carrier.

17. A pharmaceutical composition consisting essentially of a therapeutically effective amount of a compound of claim 7 and a pharmaceutically acceptable carrier.

18. A pharmaceutical composition consisting essentially of a therapeutically effective amount of a compound of claim 8 and a pharmaceutically acceptable carrier.

19. A pharmaceutical composition consisting essentially of a therapeutically effective amount of a compound of claim 9 and a pharmaceutically acceptable carrier.

20. A pharmaceutical composition consisting essentially of a therapeutically effective amount of a compound of claim 10 and a pharmaceutically acceptable carrier.

21. A method of treating lymphocytic leukemia in a mammal comprising administering to a mammal a therapeutically effective amount of a compound of claim 1.

22. A method of treating lymphocytic leukemia in a mammal comprising administering to a mammal a therapeutically effective amount of a compound of claim 2.

23. A method of treating lymphocytic leukemia in a mammal comprising administering to a mammal a therapeutically effective amount of a compound of claim 3.

24. A method of treating lymphocytic leukemia in a mammal comprising administering to a mammal a therapeutically effective amount of a compound of claim 4.

25. A method of treating lymphocytic leukemia in a mammal comprising administering to a mammal a therapeutically effective amount of a compound of claim 5.

26. A method of treating lymphocytic leukemia in a mammal comprising administering to a mammal a therapeutically effective amount of a compound of claim 6.

27. A method of treating lymphocytic leukemia in a mammal comprising administering to a mammal a therapeutically effective amount of a compound of claim 7.

28. A method of treating lymphocytic leukemia in a mammal comprising administering to a mammal a therapeutically effective amount of a compound of claim 8.

29. A method of treating lymphocytic leukemia in a mammal comprising administering to a mammal a therapeutically effective amount of a compound of claim 9.

30. A method of treating lymphocytic leukemia in a mammal comprising administering to a mammal a therapeutically effective amount of a compound of claim 10.

31. A method of treating a solid tumor in a mammal comprising administering to a mammal a therapeutically effective amount of a compound of claim 1.

32. A method of treating a solid tumor in a mammal comprising administering to a mammal a therapeutically effective amount of a compound of claim 2.

33. A method of treating a solid tumor in a mammal comprising administering to a mammal a therapeutically effective amount of a compound of claim 3.

34. A method of treating a solid tumor in a mammal comprising administering to a mammal a therapeutically effective amount of a compound of claim 4.

35. A method of treating a solid tumor in a mammal comprising administering to a mammal a therapeutically effective amount of a compound of claim 5.

36. A method of treating a solid tumor in a mammal comprising administering to a mammal a therapeutically effective amount of a compound of claim 6.

37. A method of treating a solid tumor in a mammal comprising administering to a mammal a therapeutically effective amount of a compound of claim 7.

38. A method of treating a solid tumor in a mammal comprising administering to a mammal a therapeutically effective amount of a compound of claim 8.

39. A method of treating a solid tumor in a mammal comprising administering to a mammal a therapeutically effective amount of a compound of claim 9.

40. A method of treating a solid tumor in a mammal comprising administering to a mammal a therapeutically effective amount of a compound of claim 10.

* * * * *